(12) United States Patent
Haase (10) Patent No.: US 8,221,354 B2
(45) Date of Patent: Jul. 17, 2012

(54) INFUSION DEVICE WITH POSITIVE PRESSURE ELASTIC BLADDER RESERVOIR

(75) Inventor: James Martin Haase, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 1847 days.

(21) Appl. No.: 11/412,592

(22) Filed: Apr. 27, 2006

(65) Prior Publication Data

US 2007/0255262 A1 Nov. 1, 2007

(51) Int. Cl.
*A61M 37/00* (2006.01)
(52) U.S. Cl. ............................................. 604/132
(58) Field of Classification Search .................. 604/132
See application file for complete search history.

(56) References Cited

U.S. PATENT DOCUMENTS

| | | | |
|---|---|---|---|
| 3,731,681 A | 5/1973 | Blackshear et al. | |
| 3,951,147 A | 4/1976 | Tucker et al. | |
| 4,511,355 A | 4/1985 | Franetzki et al. | |
| 4,588,394 A * | 5/1986 | Schulte et al. | 604/9 |
| 4,692,147 A | 9/1987 | Duggan | |
| 4,772,263 A | 9/1988 | Dorman et al. | |
| 5,045,064 A | 9/1991 | Idriss | |
| 5,336,180 A * | 8/1994 | Kriesel et al. | 604/82 |
| 5,820,589 A | 10/1998 | Torgerson et al. | |
| 5,840,069 A | 11/1998 | Robinson | |
| 6,036,459 A | 3/2000 | Robinson | |
| 6,554,822 B1 | 4/2003 | Holschneider et al. | |
| 6,620,151 B2 | 9/2003 | Blischak et al. | |
| 6,666,845 B2 | 12/2003 | Hooper et al. | |
| 2002/0173773 A1 | 11/2002 | Olsen | |
| 2003/0130647 A1 | 7/2003 | Gray et al. | |
| 2003/0216714 A1 | 11/2003 | Gill | |
| 2005/0024175 A1 | 2/2005 | Gray et al. | |

FOREIGN PATENT DOCUMENTS

| | | |
|---|---|---|
| WO | WO 03/039631 A1 | 5/2003 |
| WO | WO 03/099351 A * | 12/2003 |
| WO | WO 03/099351 A2 | 12/2003 |
| WO | WO 03/099351 A3 | 7/2004 |
| WO | WO 2005/002642 A2 | 1/2005 |
| WO | WO 2005/002642 A3 | 2/2005 |

OTHER PUBLICATIONS

U.S. Appl. No. 11/412,464, filed Apr. 27, 2006, Haase.
U.S. Appl. No. 11/412,375, filed Apr. 27, 2006, Haase.
U.S. Appl. No. 11/412,443, filed Apr. 27, 2006, Haase.

(Continued)

*Primary Examiner* — Nicholas Lucchesi
*Assistant Examiner* — Pritesh Patel
(74) *Attorney, Agent, or Firm* — Mueting, Raasch & Gebhardt, P.A.

(57) ABSTRACT

Implantable drug infusion devices, systems and methods for delivering therapeutic substance to a subject that include a bulkhead and an attached reservoir formed by an elastic bladder are disclosed. When filled with therapeutic substance, the elastic bladder is elastically expanded such that the therapeutic substance is held at a pressure above ambient pressure. As the therapeutic substance is removed from the reservoir, the bladder collapses and may conform to the shape of the bulkhead surface over which it is located.

26 Claims, 3 Drawing Sheets

OTHER PUBLICATIONS

"Programmable Infusion System, The SynchroMed Pump" datasheet [online]. Medtronic, Inc., Minneapolis, MN, [retrieved on May 18, 2006]. Last updated Sep. 5, 2001. Retrieved from the Internet: <URL:http://www.medtronic.com/neuro/paintherapies/pain_treatment_ladder/drug_infusion/pumps_pump_sel/synchromed_pumps.html>; 6 pgs.

"SynchroMed Infusion System: Clinical Reference Guide for Pain Therapy" [online]. Medtronic, Inc., Minneapolis, MN, [retrieved on Oct. 4, 2006]. Retrieved from the Internet: <URL: http://www.medtronic.com/neuro/paintherapies/pain_treatment_ladder/pdf/1_reference_guide.pdf>; 81 pgs.

"The Baxter Infusor, A guide for patients and their carers", Christie Hospital NHS Trust, Manchester, United Kingdom, May 2005; 12 pgs.

"The Infusor" datasheet [online]. Baxter, Deerfield, IL [retrieved from the internet on Feb. 22, 2007]. Retrieved from the internet: <URL:http://www.baxter.com/products/medication_management/infusion_pumps/elastomeric_pumps/sub/infusor.html>; 1 pg.

* cited by examiner

INFUSION DEVICE WITH POSITIVE PRESSURE ELASTIC BLADDER RESERVOIR

TECHNICAL FIELD

The present invention relates generally to drug infusion devices and, more particularly, to implantable drug infusion devices with positive pressure elastic bladder reservoirs.

BACKGROUND

Treatment of diseases and ailments of the body often benefit from short- or long-term infusion of drugs and/or other fluids. While such therapeutic substances may be administered extracorporeally, e.g., via transcutaneous injection, many patients benefit from the consistent and repeatable dosage provided by an implantable infusion pump. Such pumps may be used in a variety of applications such as control of pain and/or spasticity. They are well-suited to deliver infusate fluids to a targeted delivery site such as an epidural or intrathecal space of the spinal canal, or a particular location within the brain.

Implantable infusion pumps are typically implanted subcutaneously, e.g., in the chest or abdominal cavity. The pump may incorporate a reservoir to hold the infusate fluid. A self-sealing, needle-penetrable septum may also be provided and is preferably located generally directly beneath the skin. The septum provides a fluid passageway that permits the reservoir to be refilled periodically via a transcutaneous injection. Accordingly, the pump reservoir can be filled or refilled without requiring surgical removal from the patient's body, and further without requiring any other significant surgical procedure.

The pump may also include a discharge outlet through which the therapeutic substance is directed during delivery. The outlet is typically connected to flexible medical tubing, e.g., a catheter, leading to the targeted delivery site. In addition to the reservoir, infusion pumps may further include a power source, a pump, and associated electronics to control delivery of the therapeutic substance to the patient in accordance with a prescribed schedule.

In many implantable infusion devices, a convoluted metal bellows serves as a reservoir for a therapeutic substance. The reservoir is contained within an outer housing that contains a propellant that acts on the bellows to maintain the therapeutic substance within the reservoir at a relatively constant pressure. In some devices that pressure is negative, i.e., below ambient pressure. One example of such a device is the MIP product marketed by Medtronic-Minimed. In other devices, the pressure at which the therapeutic substance is held is positive, i.e., above ambient pressure. One example of such a device is the SYNCHROMED device marketed by Medtronic, Inc.

It has been proposed that regardless of whether the infusion devices use negative or positive pressure reservoirs, differences between the pressure in the reservoir and the ambient pressure may vary undesirably. Attempts to address this issue have included the use of flexible reservoirs that are exposed to ambient pressure. One such approach is described in International Publication No. WO 03/099351 in which a reservoir at ambient pressure is used. Such reservoirs are sometimes referred to as "neutral pressure" reservoirs.

That approach may, however, suffer from its own disadvantages. For example, the reservoir uses a flexible bladder that is designed to store the therapeutic substance to the pump at ambient pressure. At ambient pressure, the flexible membranes may allow gases within the body to pass into the therapeutic substance, potentially creating problems for the operation of the pumps used to deliver the therapeutic substance to the patient. Another potential issue is in overfill protection. The devices may require a housing within which the flexible membrane is contained to prevent over-filling—thus adding additional complexity and bulk to the device.

Yet another potential disadvantage that may be associated with neutral pressure reservoirs is that gas bubbles may form within the therapeutic substances introduced into such reservoirs. The gas bubbles are typically formed from dissolved or entrained gas in the therapeutic substance. Bubble formation may be exacerbated by the increase in temperature typically associated with implanted reservoirs held at body temperature. Gas bubbles can potentially create problems in the pump mechanisms and/or in the catheter. To address this issue, the therapeutic substance may preferably be degassed before being loaded into the reservoir, although this adds additional complexity to the loading process.

Still other issues may be raised in connection with infusion devices that use peristaltic pumps to deliver a therapeutic substance from a reservoir to a catheter. Neutral pressure reservoirs may not provide sufficient fluid to adequately feed the inlet to a peristaltic pump. In some cases, the peristaltic pump tube may collapse at the pump inlet due to insufficient pressure to maintain the pump tube filled with the therapeutic substance. In devices that include a reservoir pressurized above ambient pressure (using, e.g., a propellant), the reservoir pressure may be undesirably increased due to temperature increases, changes in altitude, etc.

As the reservoir pressure increases, the occluding force applied to the pump tube may need to be increased to address reservoir-pressure induced leakage through the occluded portion of the pump tube. Frequently, the peristaltic pumps in such infusion devices are assembled in a significantly over-occluded state to ensure sufficient occlusion forces at all points on the pump tube. On the other hand, over-occlusion (excessive compressive load on the tube) is undesirable because it results in unnecessary friction and leads to increased wear and excessive power consumption by the pump drive system. Excessive power consumption is particularly undesirable in the field of implantable, battery-powered infusion devices. Over-occlusion results in increased cyclic loading of the pump tube and thus reduces the tube leakage safety margin and useful life. Similarly, over-occlusion results in unnecessary wear on the pump rollers, bearings and other components.

SUMMARY OF THE INVENTION

The present invention provides implantable drug infusion devices for delivering therapeutic substance to a subject that include a bulkhead and an attached reservoir formed by an elastic bladder. When filled with therapeutic substance, the elastic bladder is preferably elastically expanded such that the therapeutic substance is held at a pressure above ambient pressure. As the therapeutic substance is removed from the reservoir, the bladder collapses and preferably conforms to the shape of the bulkhead surface over which it is located.

One potential advantage of the present invention is that, by holding the therapeutic substance at a positive pressure (i.e., above ambient pressure), dissolved gases in the body in which the device is implanted will be less likely to pass into the therapeutic substance in the reservoir. In some instances, dissolved gases in the therapeutic substance may even pass out of the therapeutic substance into the surrounding anatomy if at least a portion of the elastic bladder is gas-permeable such that gases within the therapeutic substance can pass out of the reservoir. Such degassing in the reservoir of the infusion device may reduce or eliminate the need to actively degass the therapeutic substance before delivering it to the reservoir.

In addition to the potential for degassing the therapeutic substance, those embodiments of implantable drug infusion devices that include a peristaltic pump may also find advantages in maintaining an adequate inflow of therapeutic substance into the inlet of the peristaltic pump due to the positive pressure imparted by the elastic bladder.

Another potential advantage is that the elastic bladder can conform to an irregular reservoir surface on the bulkhead. In some instances, the reservoir surface of the bulkhead may be asymmetric. By freeing the design from the constraint of requiring a flat surface on the portion of the bulkhead that faces the reservoir, the overall size of the infusion device may be reduced because the components (e.g., pump, battery, etc.) may be placed to improve packing density without regard to their effect on the shape of the reservoir surface. In some instances, the elastic bladder may be molded in the shape of the reservoir surface.

Another potential advantage of embodiments of the present invention including a peristaltic pump to deliver therapeutic substance is that the level of occluding force needed to prevent leakage past the occluded portion of the tube may be reduced as compared to infusion devices using propellant-driven reservoirs. The occluding force may be reduced because the reduced reservoir pressure (and, thus, pump inlet pressure) may decrease the amount of occluding force necessary to prevent leakage through the occluded portions of the pump tube. As a result, the torque (and, therefore, the power) required to operate the pump rotor could be reduced as the reservoir pressure decreases. Reductions in energy consumption may be particularly beneficial in implantable infusion devices in which power is supplied by a battery or other finite energy source.

Another potential advantage of the present invention is that the flexibility and elasticity of the elastic bladder used to form the reservoir may reduce the issues associated with overfilling of the reservoir. In other words, limited overfilling will not typically lead to a rapid rise in pressure within the reservoir.

Another potential advantage of the present invention is that the reservoir portion of the infusion device is smooth and flexible—which can potentially improve patient comfort.

Another potential advantage so the present invention is that, in some instances, the material used for the elastic bladder will exhibit a self-sealing function similar to that of a septum. As a result, if unintentionally pierced by a needle, the elastic bladder may still retain the therapeutic substance without significant leakage.

In one aspect, the present invention provides an implantable medical device for the infusion of a therapeutic substance into an anatomy, the medical device including a bulkhead with an electrical power source, a pump operably connected to the electrical power source, and a reservoir surface; an elastic bladder attached to the bulkhead over the reservoir surface, wherein the elastic bladder and the reservoir surface define an interior volume of a reservoir, wherein the elastic bladder is exposed to ambient pressure outside of the medical device, wherein the elastic bladder elastically deforms when loaded with therapeutic substance such that the therapeutic substance is pressurized above ambient pressure, and wherein at least a portion of the elastic bladder is gas-permeable such that gas within the therapeutic substance can pass out of the reservoir through the elastic bladder; a pump port operably connecting an inlet of the pump to the interior volume of the reservoir; and an outlet port through which the therapeutic substance is pumped out of the medical device using the pump.

In another aspect, the present invention provides an implantable medical device for the infusion of a therapeutic substance into an anatomy, the medical device including a bulkhead with an electrical power source, a pump operably connected to the electrical power source, and an asymmetric reservoir surface; an elastic bladder attached to the bulkhead over the reservoir surface, wherein the elastic bladder consists essentially of elastomeric silicone, wherein the elastic bladder and the reservoir surface define an interior volume of a reservoir, wherein the elastic bladder is exposed to ambient pressure outside of the medical device, wherein the elastic bladder elastically deforms when loaded with therapeutic substance such that the therapeutic substance is pressurized above ambient pressure, and wherein at least a portion of the elastic bladder is gas-permeable such that gas within the therapeutic substance can pass out of the reservoir through the elastic bladder, and further wherein the elastic bladder conforms to the asymmetric reservoir surface when the internal volume of the reservoir is at ambient pressure; a pump port operably connecting an inlet of the pump to the interior volume of the reservoir; and an outlet port through which the therapeutic substance is pumped out of the medical device using the pump.

In another aspect, the present invention provides a implantable medical device for the infusion of a therapeutic substance into an anatomy, the medical device including a bulkhead with an electrical power source, a peristaltic pump operably connected to the electrical power source, and a reservoir surface; an elastic bladder attached to the bulkhead over the reservoir surface, wherein the elastic bladder and the reservoir surface define an interior volume of a reservoir, wherein the elastic bladder is exposed to ambient pressure outside of the medical device, and wherein the elastic bladder elastically deforms when loaded with therapeutic substance such that the therapeutic substance is pressurized above ambient pressure; a pump port operably connecting an inlet of the pump to the interior volume of the reservoir; and an outlet port through which the therapeutic substance is pumped out of the medical device using the pump.

In another aspect, the present invention provides a method of operating an implantable therapeutic substance device. The method includes providing an implantable medical device for the infusion of a therapeutic substance into an anatomy, the medical device including a bulkhead with an electrical power source, a pump operably connected to the electrical power source, and a reservoir surface; an elastic bladder attached to the bulkhead over the reservoir surface, wherein the elastic bladder and the reservoir surface define an interior volume of a reservoir, wherein the elastic bladder is exposed to ambient pressure outside of the medical device; a pump port operably connecting an inlet of the pump to the interior volume of the reservoir; and an outlet port through which the therapeutic substance is pumped out of the medical device using the pump. The method further includes delivering therapeutic substance to the inlet of the pump using positive pressure in the reservoir, wherein the positive pressure is the result of elastic deformation of the elastic bladder by the therapeutic substance located therein; and pumping the therapeutic substance out of the medical device through the outlet port using the pump. In various aspects, the methods may further include degassing the therapeutic substance after it is located in the reservoir. The pumps used in the methods may be, e.g., piston pumps, peristaltic pumps, etc.

The above summary is not intended to describe each embodiment or every implementation of the present invention. Nor are all of the potential features and advantages of the present invention included. Rather, a more complete understanding of the invention will become apparent and appreciated by reference to the following Detailed Description of Exemplary Embodiments and claims in view of the accompanying figures of the drawing.

BRIEF DESCRIPTION OF THE VIEWS OF THE DRAWING

The present invention will be further described with reference to the figures of the drawing.

DETAILED DESCRIPTION OF EXEMPLARY EMBODIMENTS

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

The present invention is directed to medical devices and, in particular, to infusion devices and systems that are implanted within a patient's body. Infusion devices in accordance with embodiments of the present invention typically incorporate an elastic bladder that elastically deforms when loaded with a therapeutic substance. Elastic deformation of the bladder places the therapeutic substance therein under positive pressure with respect to ambient pressure. Corresponding methods for dispensing a the therapeutic substance to the body via the medical device are also contemplated.

The term "elastic" (and variations thereof) as used herein describes the physical properties of an article wherein, when elastically deformed (e.g., elongated), the article substantially resumes its original shape within a period of two minutes or less.

It is noted that the terms "comprises" and variations thereof do not have a limiting meaning where these terms appear in the accompanying description and claims. Moreover, "a", "an", "the", "at least one", and "one or more" are used interchangeably herein.

Relative terms such as left, right, forward, rearward, top, bottom, side, upper, lower, horizontal, vertical, and the like may be used herein and, if so, are from the perspective observed in the particular figure. These terms are used only to simplify the description, however, and not to limit the scope of the invention in any way.

Figure 1:
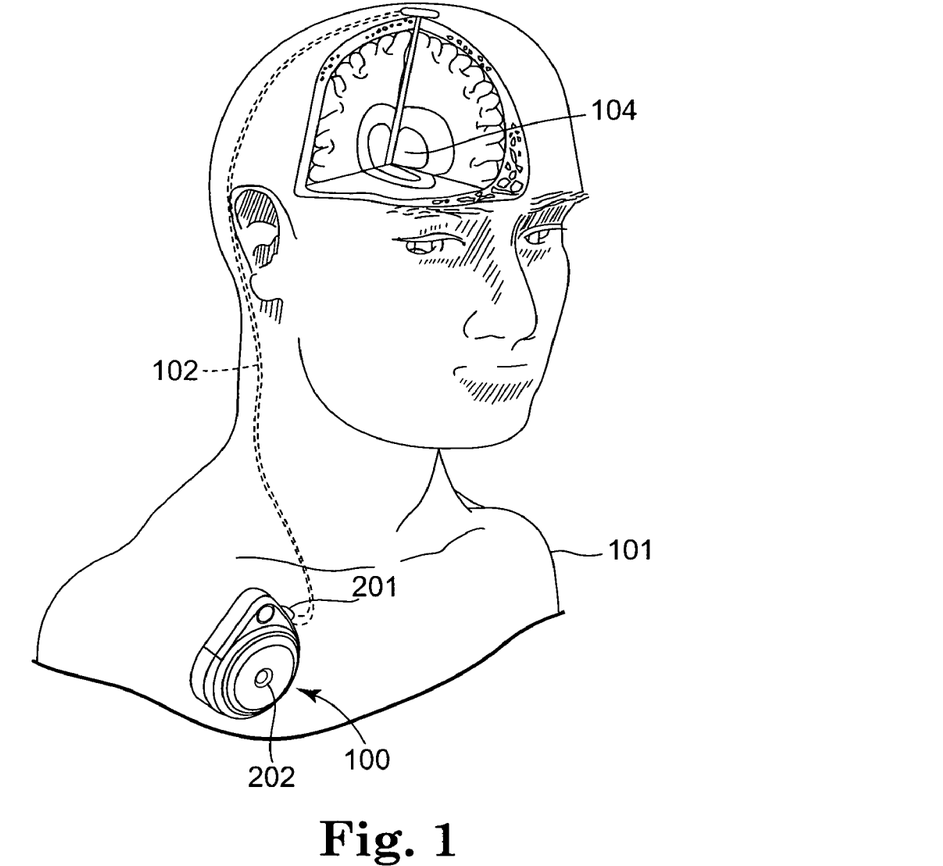
FIG. 1 illustrates an exemplary medical system, e.g., implantable infusion system, as it may be implanted in a patient's body, wherein the system incorporates an active infusion device in accordance with one embodiment of the present invention.
Figure 2:
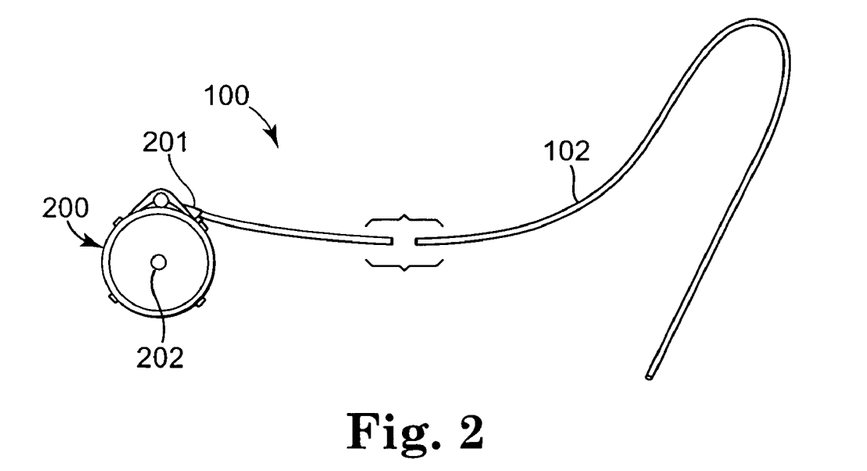
FIG. 2 is a view of the infusion system of FIG. 1 removed from the body.

FIGS. 1 and 2 illustrate an implantable medical system, such as a therapeutic substance infusion system 100, in accordance with one embodiment of the invention (FIG. 1 illustrates the system 100 as it may be implanted within the patient's body 101, while FIG. 2 illustrates the system isolated, i.e., outside the body). The exemplary infusion system includes a medical device, e.g., implantable medical device 200, and preferably at least one catheter 102. Such systems may be used for a wide variety of therapies including treatment of pain, spasticity, and other medical conditions.

The device 200 and catheter 102 are typically implanted by a clinician (e.g., surgeon) within the body 101 during a surgical procedure. While the present invention also contemplates embodiments wherein the catheter is implanted with one end outside the body so that it may attach to an external infusion device, the remainder of this description is, for the sake of brevity, directed to implantable medical systems.

Before implantation of the device 200, the catheter 102 may be positioned with its distal end (i.e., the end that does not couple to the device) located at a desired therapy delivery site 104 within the body 101, e.g., within the brain (while shown as delivering a therapeutic substance to a site 104 within the brain, the distal end of the catheter 102 may be located at most any location within the body 101, e.g., an epidural or intrathecal space of the spinal canal). A proximal end of the catheter 102 may be tunneled through the tissue to the device implant location and coupled to a catheter or outlet port 201 of the device 200. The device 200 is typically implanted subcutaneously, e.g., about 2.5 cm (1 inch) beneath the skin, where there is sufficient tissue for supporting the device, e.g., with sutures or the like.

The device 200 is, in the illustrated embodiment, operable to infuse a therapeutic substance (also referred to as "drug" herein) from an enclosed substance or drug reservoir 202 into the body 101. The "therapeutic substance" may be a substance intended to have a therapeutic effect on the patient, e.g., pharmaceutical compositions, genetic materials, biologics, and other substances.

"Pharmaceutical compositions," as used herein, may include chemical formulations intended to have a therapeutic effect such as intrathecal antispasmodics, pain medications, chemotherapeutic agents, and the like. Pharmaceutical compositions are often configured to function effectively in an implanted environment by possessing various characteristics including: stability at body temperature to retain therapeutic qualities; concentration to reduce the frequency of replenishment; and the like. "Genetic materials," as used herein, may include substances intended to have a direct or indirect genetic therapeutic effect such as genetic vectors, genetic regulator elements, genetic structural elements, DNA, and the like. "Biologics," as used herein, may include substances that are living matter, or derived from living matter, and offer a therapeutic effect to the patient such as stem cells, platelets, hormones, biologically produced chemicals, and the like. "Other substances" may include most any other substance that is intended to have a therapeutic effect, yet does not clearly fit within one of the categories identified above. Examples of other substances may include saline solutions, fluoroscopy agents, and the like.

In some embodiments, the therapeutic substance contained within a reservoir of the infusion device 200 may be replenished periodically after device implantation. Typically, replenishment is accomplished with a non-coring needle (not shown) connected to a syringe filled with the therapeutic substance. The needle may be inserted through the patient's skin and into a self-sealing septum 204 of the device 200.

Figure 3:
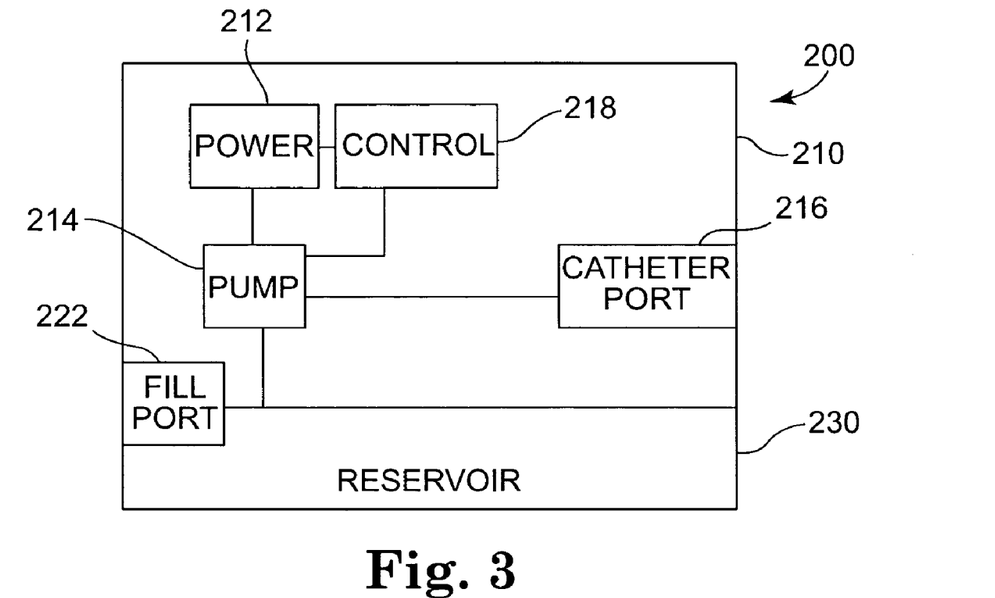
FIG. 3 is a schematic block diagram of one infusion device according to the present invention.

FIG. 3 is a schematic diagram of one exemplary embodiment of the infusion device 200. As shown in the diagram, the infusion device 200 may include a bulkhead 210 that encloses various components in the device 200. Those components located within the bulkhead 210 may include, e.g., an electric power source 212 (e.g., battery, capacitor, etc.). The bulkhead 210 may also house a pump 214 operably connected to receive power from the power source 212. The pump 214 may preferably be connected to a catheter port 216 such that the pump 214 can deliver the therapeutic substance to the catheter port 216 for infusion in the patient.

Many different pumps may alternatively be used in the infusion devices of the present invention, including, but not limited to, peristaltic pumps, solenoid pumps, diaphragm pumps, piston pumps, piezoelectric pumps, etc. Examples of some potentially suitable pumps that may be used in connection with the infusion device 200 may be described in U.S. Patent Application Publication No. 2003/0130647 A1 (Gray et al.), titled INFUSION DEVICE AND DRIVING MECHANISM FOR SAME; U.S. Patent Application Publication No. 2005/0024175 A1 (Gray et al.), titled INFUSION DEVICE AND DRIVING MECHANISM AND PROCESS FOR SAME WITH ACTUATOR FOR MULTIPLE INFUSION USES; and U.S. Patent Application Publication No. US 2002/0173773 A1 (Olsen), titled PERMANENT MAGNET SOLENOID PUMP FOR AN IMPLANTABLE THERAPEUTIC SUBSTANCE DELIVERY DEVICE; as well as in U.S. Pat. No. 4,692,147 (Duggan).

The bulkhead 210 may also include control electronics 218 operably connected to the power source 212 and the pump 214. The control electronics 218 may preferably include memory and a controller. The controller may be an Application Specific Integrated Circuit (ASIC) state machine, a gate array, and/or may include a microprocessor. The control electronics 218 are preferably configured to operate the pump 214 (e.g., controlling infusion rate, etc.). The control electronics 218 may also include components, etc. to operate other features such as valves, sensors (temperature, density, etc.), patient alarms, etc. The control electronics 218 may also include telemetry components configured to receive and/or send information after the infusion device 200 is implanted in a patient. Telemetry may be used to, e.g., allow programming of the infusion rate, infusion times, etc. Telemetry may also be used to provide information from the infusion device such as, e.g., the amount of therapeutic substance in the reservoir, etc. Such information may be used to determine whether the reservoir requires refilling, etc.

Also depicted in FIG. 3 is a fill port 222 located in the bulkhead 210. The fill port 222 may take the form of, e.g., a septum, etc. Other components not specifically depicted in FIG. 3 may also be included in the bulkhead 210, e.g., valves to control fluid flow, overfill protection devices, etc.

The infusion device 200 also preferably includes a reservoir 230 attached to the bulkhead 210. The reservoir is preferably in fluid communication with both the fill port 222 such that a therapeutic substance can be delivered into the reservoir 230 through the fill port 222. Although described as a fill port, it should be understood that the fill port 222 may alternatively be used to remove fluids such as therapeutic substances, air, etc. from the reservoir in addition to or in place of delivering fluid into the reservoir 230.

The reservoir 230 is also preferably in fluid communication with the inlet side of the pump 214. As a result, therapeutic substance in the reservoir 230 can be supplied to the pump 214 for infusion into a patient as discussed herein. Although not depicted, one or more valves may be used to control delivery fluid from the reservoir 230 to the pump 214. The reservoir 230 is preferably formed using an elastic bladder that conforms to the shape of the bulkhead 210 when empty.

As discussed herein, it is also preferred that therapeutic substance loaded into the reservoir 230 is held at pressure above ambient pressure, with the force required to generate that positive pressure being supplied by elastic deformation of at least a portion of the reservoir 230 (in addition to ambient pressure acting on the reservoir 230). In embodiments in which the pump 214 is a peristaltic pump, it may be preferred that the positive pressure exerted on the therapeutic substance in the reservoir 230 (and, thus, on the inlet side of the pump 214), be limited to, e.g., 5 psi (about 35 kPa) or less. Limiting the reservoir pressure may provide advantages in operation of a peristaltic pump such as, e.g., reduced occluding forces, reduced power consumption, etc.

Figure 4:
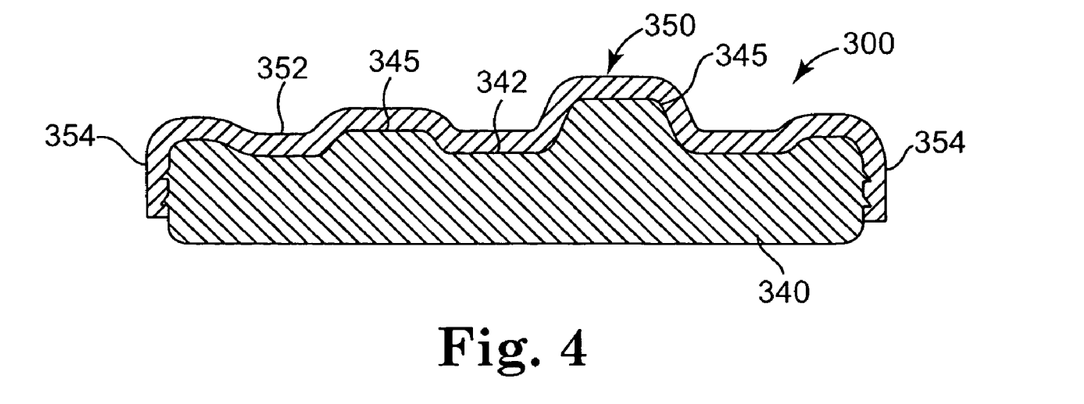
FIG. 4 is a simplified cross-sectional view of one infusion device according to the present invention to illustrate the conformance of the elastic bladder to the reservoir surface in the absence of therapeutic substance in the reservoir.
Figure 5:
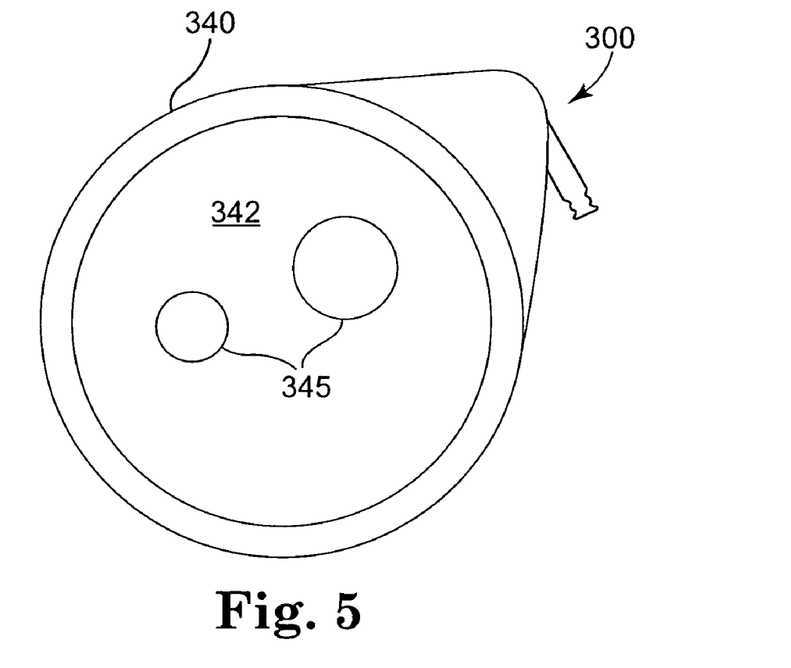
FIG. 5 is a plan view of the simplified reservoir surface of the infusion device of FIG. 4.
Figure 6:
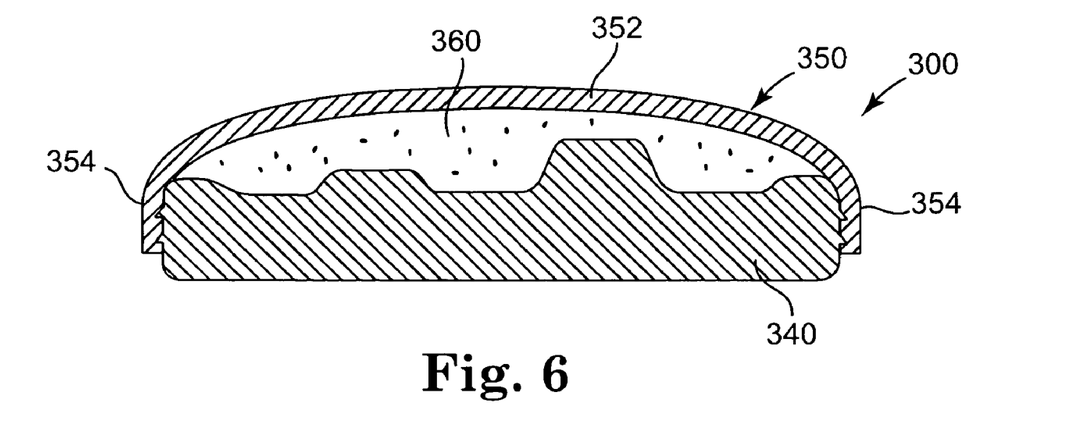
FIG. 6 is a simplified cross-sectional view of the infusion device of FIG. 4 with therapeutic substance in the reservoir in an amount sufficient to elastically deform the bladder such that it is raised from the reservoir surface.

FIGS. 4-6 depict one exemplary bulkhead 340 and associated elastic bladder 350 used to form a reservoir of the infusion device 300 to illustrate at least some of the principles of the present invention. FIG. 4 is a cross-sectional view of the infusion device simplified to include only the shape of the bulkhead 340 and the elastic bladder 350 (the components located within the bulkhead 340 are not depicted to simplify the figure).

The bulkhead 340 preferably includes a reservoir surface 342 that faces the elastic bladder 350. Unlike known infusion devices, the reservoir surface 342 over which the elastic bladder 350 is located need not be flat. Rather, the elastic bladder 350 preferably conforms to the irregular reservoir surface 342 when the reservoir is empty or nearly empty of any therapeutic substance (as depicted in FIG. 4.

The reservoir surface 342 depicted in FIGS. 4-6 includes features 345 that protrude from the base portion 346 of the surface 342. The features 345 may be formed by any number of a variety of components located in the bulkhead such as, for example, the power source, pump, control electronics, etc. In conventional infusion devices using, e.g., a bellows for the reservoir, the surface of the device facing the bellows is typically flat or featureless to promote emptying of the reservoir as the bellows collapses. Other infusion devices may use reservoirs with Belleville washers or similar structures that collapse as the reservoir is emptied. Those infusion devices, however, typically require that the surface against which the reservoir collapses exhibit symmetry in two or more planes.

At least some of the infusion devices of the present invention, however, include a reservoir formed by an elastic bladder that preferably provides positive pressure on the therapeutic substance while collapsing against an irregular reservoir surface. One potential advantage of an irregular reservoir surface is that the overall volume and size of the infusion device may be reduced because additional volume is not required in attempting to provide a flat surface for the reservoir.

The reservoir surface 342 may, in some embodiments, be asymmetric. As used herein, an "asymmetric reservoir surface" is a reservoir surface that is shaped such that no planes of symmetry exist that intersect the reservoir surface in a direction generally normal to the reservoir surface (orifices used to deliver or remove therapeutic substances to or from the reservoir are not considered in determining asymmetry). Examples of planes that intersect the reservoir surfaces in directions generally normal to the reservoir surfaces may be seen in the paper on which FIGS. 4 and 6 are printed. This asymmetry is in contrast with infusion devices that include bulkheads with reservoir surfaces that exhibit multiple, if not infinite, numbers of planes of symmetry (see, e.g., U.S. Pat. No. 4,772,263 to Dorman et al. and International Publication No. WO 03/099351 to Lord et al.).

The reservoirs in the infusion devices of the present invention are formed using elastic bladders. One example of such a bladder 350 is depicted in FIGS. 4 and 6 (the bladder in FIG. 5 being removed to expose the underlying reservoir surface 342). The elastic bladder 350 is depicted in FIG. 6 in its expanded condition in which therapeutic substance 360 elastically deforms the bladder 350 such that the therapeutic substance 360 is pressurized above ambient pressure by the force exerted on the therapeutic substance 360 by the elastically deformed bladder 350.

The bladder 350 may be in the form of a molded elastomeric cup that includes a base 352 facing the reservoir surface 342 and a sidewall 354 connecting the base to the bulkhead 340. The cup-shaped elastic bladder 350 forming the reservoir may preferably be generally circular to match the circular shape of the reservoir surface 342, although it should be understood that the reservoir surface and corresponding elastic bladder may take other shapes, such as e.g., oval, elliptical, pentagonal, hexagonal, etc. Although in some embodiments, the shape of the reservoir surface 342 and the base 352 of the cup-shaped elastic bladder 350 may match, in other embodiments the shape of the reservoir surface 342 and the base 352 of the cup-shaped elastic bladder 350 may be different. For example, the base of the cup-shaped bladder 350 may be generally circular while the shape of the reservoir surface is pentagonal, hexagonal, elliptical, oval, etc. In such instances, the flexibility and elasticity of the elastic bladder may allow it to adequately conform to the different shape of the reservoir surface 342.

The elastic bladder 350 may be formed of a variety of materials. Suitable materials, will, however, exhibit sufficient elasticity and flexibility to allow adequate filling of the reservoir with a therapeutic substance 360 as depicted in FIG. 6. When filled, the elastic bladder 350 expands to accommodate the volume of the therapeutic substance 360. Because of the elasticity of the bladder 350, the therapeutic substance 360 within the reservoir is held under positive pressure (i.e., at a pressure greater than ambient pressure). At the same, time, the positive pressure exerted by the elastic bladder 350 is adjusted by the ambient pressure exerted in the exterior of the bladder 350 (the surface of the bladder facing away from the therapeutic substance 360). As ambient pressure increases, the pressure of the therapeutic substance 360 within the reservoir increases. Likewise, as ambient pressure decreases, the pressure of the therapeutic substance 360 decreases.

As discussed herein, holding the therapeutic substance 360 under positive pressure with respect to ambient pressure may provide advantages in the degassing of the therapeutic substance 360 located within the elastic bladder 350. The elastic bladder 350 (or at least a portion thereof) may preferably be gas-permeable such that gases within the therapeutic substance 360 are urged to pass out of the reservoir through the gas-permeable bladder portions. In addition, because the therapeutic substance 360 is held at a pressure above ambient pressure, the passage of gases from the environment in which the infusion device 300 is located into the therapeutic substance 360 may be reduced or prevented.

As depicted in FIGS. 4-6, the bulkhead 340 may also include barbs 344 or other features located around the outer perimeter 346 of the reservoir surface 342 to assist in securing the elastic bladder 350 to the bulkhead 340. The use of barbs or similar structures may advantageously rely in the elastic nature of the sidewall 354 of the bladder 350 to provide a secure, fluid-tight attachment between the bladder 350 and the bulkhead 340. The attachment of the bladder 350 to the bulkhead 340 may be enhanced by the use of clamps, adhesives, etc.

Suitable materials for the elastic bladders used in connection with the present invention may preferably possess a number of characteristics including, but not limited to: biocompatibility, elasticity, flexibility, drug-compatibility, etc. Some potentially suitable elastomeric materials that may be used to construct the bladders may include, e.g., silicones, urethanes, etc. In some instances, the elastic bladders may consist essentially of elastomeric polymeric material, e.g., the elastic bladder may consist essentially of elastomeric silicone.

Although the elastic bladder 350 depicted in FIGS. 4 and 6 is illustrated as a homogeneous, single-layer structure, elastic bladders used in connection with the present invention may alternatively take on a variety of different constructions, with multi-layer composites, different materials located in different areas (e.g., variations between the base and the sidewall, etc.).

Construction of the elastic bladders may be accomplished by any suitable technique or techniques. It may be preferred that the elastic bladder be constructed as a molded polymeric article, where molding includes casting, extrusion forming, etc. If molded, the base of a cup-shaped elastic bladder used in connection with the present invention may be molded in a shape that conforms to the irregular shape of a reservoir surface over which the elastic bladder is to be used.

Regardless of the exact technique or techniques used to construct and attach the elastic bladders of the present invention, it may be preferred that, in their relaxed state (i.e., in the absence of sufficient therapeutic substance or other fluid materials), the elastic bladders conform to the reservoir surfaces over which they are located.

A potential advantage in the use of silicone for an elastic bladder in connection with the present invention is that silicone hydrates while implanted in a living body. That hydration may help the connection between the elastic bladder and the bulkhead to remain fluid-tight while implanted.

The complete disclosure of the patents, patent documents, and publications cited in the Background, the Detailed Description of Exemplary Embodiments, and elsewhere herein are incorporated by reference in their entirety as if each were individually incorporated.

Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. An implantable medical device for the infusion of a therapeutic substance into an anatomy, the medical device comprising:
 a bulkhead comprising an electrical power source, a pump operably connected to the electrical power source, and an asymmetric reservoir surface;
 an elastic bladder attached to the bulkhead over the reservoir surface, wherein the elastic bladder and the reservoir surface define an interior volume of a reservoir, wherein the elastic bladder is exposed to ambient pressure outside of the medical device, wherein the elastic bladder elastically deforms when loaded with therapeutic substance such that the therapeutic substance is pressurized above ambient pressure, and wherein the elastic bladder conforms to the reservoir surface of the bulkhead when the internal volume of the reservoir is at ambient pressure;

a pump port operably connecting an inlet of the pump to the interior volume of the reservoir; and an outlet port through which the therapeutic substance is pumped out of the medical device using the pump.

2. A device according to claim 1, wherein the elastic bladder comprises a cup-shape comprising a base facing the reservoir surface of the bulkhead and a sidewall extending between the base and the bulkhead.

3. A device according to claim 2, wherein the sidewall extends over a perimeter of the bulkhead, wherein elastic deformation of the sidewall of the elastic bladder seals the elastic bladder against the perimeter of the bulkhead.

4. A device according to claim 2, wherein the perimeter of the bulkhead comprises one or more barb structures, and wherein the sidewall of the elastic bladder is stretched over the one or more barb structures.

5. A device according to claim 1, wherein the elastic bladder comprises a molded polymeric article.

6. A device according to claim 1, wherein the elastic bladder consists essentially of elastomeric polymeric material.

7. A device according to claim 1, wherein the elastic bladder consists essentially of elastomeric silicone.

8. An implantable medical device for the infusion of a therapeutic substance into an anatomy, the medical device comprising:

a bulkhead comprising an electrical power source, a pump operably connected to the electrical power source, and an asymmetric reservoir surface;

an elastic bladder attached to the bulkhead over the reservoir surface, wherein the elastic bladder consists essentially of elastomeric silicone, wherein the elastic bladder and the reservoir surface define an interior volume of a reservoir, wherein the elastic bladder is exposed to ambient pressure outside of the medical device, wherein the elastic bladder elastically deforms when loaded with therapeutic substance such that the therapeutic substance is pressurized above ambient pressure, and wherein the elastic bladder comprises gas-permeable material such that gas within the therapeutic substance can pass out of the reservoir through the gas permeable material, and further wherein the elastic bladder conforms to the asymmetric reservoir surface when the internal volume of the reservoir is at ambient pressure;

a pump port operably connecting an inlet of the pump to the interior volume of the reservoir; and an outlet port through which the therapeutic substance is pumped out of the medical device using the pump.

9. A device according to claim 8, wherein the elastic bladder comprises a cup-shape comprising a base facing the reservoir surface of the bulkhead and a sidewall extending between the base and the bulkhead.

10. A device according to claim 9, wherein the sidewall extends over a perimeter of the bulkhead, wherein elastic deformation of the sidewall of the elastic bladder seals the elastic bladder against the perimeter of the bulkhead.

11. A device according to claim 9, wherein the perimeter of the bulkhead comprises one or more barb structures, and wherein the sidewall of the elastic bladder is stretched over the one or more barb structures.

12. A device according to claim 8, wherein the elastic bladder comprises a molded polymeric article.

13. A device according to claim 8, wherein the elastic bladder consists essentially of elastomeric polymeric material.

14. A device according to claim 8, wherein the elastic bladder consists essentially of elastomeric silicone.

15. A device according to claim 1, wherein the asymmetric reservoir surface comprises a feature that protrudes from a base portion of the reservoir surface, wherein the feature that protrudes from the base portion is formed by one of the electrical power source and the pump.

16. A device according to claim 8, wherein the asymmetric reservoir surface comprises a feature that protrudes from a base portion of the reservoir surface, wherein the feature that protrudes from the base portion is formed by one of the electrical power source and the pump.

17. A device according to claim 1, wherein the elastic bladder is at ambient pressure when the reservoir is empty.

18. A device according to claim 8, wherein the elastic bladder is at ambient pressure when the reservoir is empty.

19. An implantable medical device for the infusion of a therapeutic substance into an anatomy, the medical device comprising:

a bulkhead comprising an electrical power source, a pump operably connected to the electrical power source, and an irregular reservoir surface, wherein the irregular reservoir surface comprises a feature that protrudes from a base portion of the reservoir surface, wherein the feature that protrudes from the base portion is formed by one of the electrical power source and the pump;

an elastic bladder attached to the bulkhead over the reservoir surface, wherein the elastic bladder and the reservoir surface define an interior volume of a reservoir, wherein the elastic bladder is exposed to ambient pressure outside of the medical device, wherein the elastic bladder elastically deforms when loaded with therapeutic substance such that the therapeutic substance is pressurized above ambient pressure, and wherein the elastic bladder conforms to the irregular reservoir surface of the bulkhead when the reservoir is empty;

a pump port operably connecting an inlet of the pump to the interior volume of the reservoir; and an outlet port through which the therapeutic substance is pumped out of the medical device using the pump.

20. A device according to claim 19, wherein the irregular reservoir surface is asymmetric.

21. A device according to claim 19, wherein the internal volume of the reservoir is at ambient pressure when the reservoir is empty.

22. A device according to claim 19, wherein the elastic bladder comprises a cup-shape comprising a base facing the reservoir surface of the bulkhead and a sidewall extending between the base and the bulkhead.

23. A device according to claim 22, wherein the sidewall extends over a perimeter of the bulkhead, wherein elastic deformation of the sidewall of the elastic bladder seals the elastic bladder against the perimeter of the bulkhead.

24. A device according to claim 22, wherein the perimeter of the bulkhead comprises one or more barb structures, and wherein the sidewall of the elastic bladder is stretched over the one or more barb structures.

25. A device according to claim 19, wherein the elastic bladder comprises a molded polymeric article.

26. A device according to claim 19, wherein the elastic bladder consists essentially of elastomeric polymeric material.

* * * * *